United States Patent [19]

Carter

[11]B 4,014,917
[45] Mar. 29, 1977

[54] AMINOMETHYLENEMALONITRILES
[75] Inventor: Peter Laurence Carter, Bishop's Stortford, England
[73] Assignee: Fisons Limited, England
[22] Filed: Oct. 3, 1973
[21] Appl. No.: 403,076
[44] Published under the record Trial Voluntary Protest Program on April 13, 1976 as document No. 403,076.
[30] Foreign Application Priority Data
Oct. 6, 1972 United Kingdom ............ 46180/72
[52] U.S. Cl. .................. 260/465 E; 260/294.8 E; 260/294.9; 260/304 R; 260/309.2; 260/455 A; 260/465 D; 260/465.4; 260/465.5 R; 424/263; 424/270; 424/273; 424/301; 424/304
[51] Int. Cl.² ...................................... C07C 121/78
[58] Field of Search .............................. 260/465 E
[56] References Cited
UNITED STATES PATENTS
3,309,396 3/1967 Shulgin ........................... 260/465 X
3,551,573 12/1970 Baker et al. .................... 260/465 X

*Primary Examiner*—Lewis Gotts
*Assistant Examiner*—Dolph H. Torrence
*Attorney, Agent, or Firm*—Wenderoth, Lind & Ponack

[57] ABSTRACT

Compounds of formula

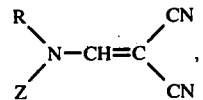

wherein R is substituted- or unsubstituted- aryl, alkyl, aralkyl or heterocyclic linked via a carbon atom in the heterocycle and Z is trichloromethylthio, dichlorofluoromethylthio,

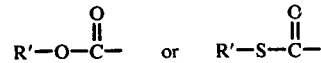

where R' is substituted- or unsubstituted- alkyl, aryl or aralkyl, are fungicides, especially for combating fungal diseases of plants eg vines.

8 Claims, No Drawings

AMINOMETHYLENEMALONITRILES

The present invention relates to fungicidal compounds, their preparation, their use and fungicidal compositions containing them.

The invention provides an aminomethylenemalononitrile compound of general formula:

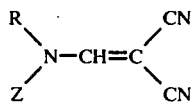 (I)

in which R represents aryl (for example phenyl or naphthyl), substituted aryl (for example phenyl or naphthyl substituted by one or more substituents selected from halogen, alkyl of 1–4 carbon atoms and alkoxy of 1–4 carbon atoms, such as chlorophenyl, methylphenyl, dimethylphenyl or methoxyphenyl), alkyl (for example of 1–16 carbon atoms such as methyl, isopropyl or tridecyl), substituted alkyl (for example the alkyl substituted by one or more substituents selected from alkoxy of 1–4 carbon atoms, nitro and halogen, such as methoxypropyl, nitroethyl or chloroethyl), aralkyl (for example phenylalkyl such as benzyl or phenylethyl), substituted aralkyl (for example benzyl or phenylethyl whose phenyl group is substituted by one or more substituents selected from halogen and alkyl of 1–4 carbon atoms), a heterocyclic group (for example pyridyl, benzothiazolyl or benzimidazolyl) linked via a carbon atom in the group or a substituted heterocyclic group linked via a carbon atom in the group (for example the heterocyclic group substituted by one or more substituents selected from halogen and alkyl of 1–4 carbon atoms, such as chloropyridyl or methylpyridyl); and Z represents trichloromethylthio, dichlorofluoromethylthio

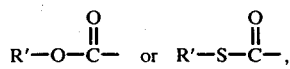

where R' represents alkyl (for example of 1–6 carbon atoms such as methyl, ethyl or isopropyl), substituted alkyl (for example the alkyl substituted by one or more substituents selected from halogen and alkoxy of 1–4 carbon atoms, such as chloroethyl or methoxypropyl), aryl (for example phenyl or naphthyl), substituted aryl (for example phenyl or naphthyl substituted by one or more substituents selected from alkyl of 1–4 carbon atoms, alkoxy of 1–4 carbon atoms and halogen, such as tolyl, xylyl, methoxyphenyl, chlorophenyl or dichlorophenyl), aralkyl (for example phenylalkyl such as benzyl or phenylethyl) or substituted aralkyl (for example benzyl or phenylethyl whose phenyl group is substituted by one or more substituents selected from halogen and alkyl of 1–4 carbon atoms).

The invention also provides a process for preparing the compound, which process comprises reacting an aminomethylenemalononitrile derivative of formula

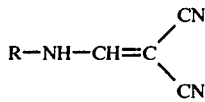 (II)

with a halide of formula ZX in the presence of a base, or a salt of the derivative with the halide, where R and Z are as defined above and X represents a halogen atom.

The invention provides also a fungicidal composition containing the compound, in particular a solid fungicidal composition comprising the compound together with a solid carrier, a liquid fungicidal composition comprising the compound together with a liquid carrier which is a hydrocarbon which boils within the range 130°–270° C, a fungicidal composition comprising the compound together with a surface active agent, and a fungicidal composition comprising the compound together with another pesticide.

In addition, the invention provides a method of combating fungus at a locus infested or liable to be infested with it, which method comprises applying to the locus a fungus-combating amount of the compound.

In the compounds of formula I, when R or R' represents a substituted aryl group, it is usually aryl mono- or di-substituted, and similarly when R represents the substituted heterocyclic group it is usually the heterocyclic group mono- or di-substituted and when R or R' represents a substituted aralkyl group it is usually the aralkyl group mono- or di-substituted; when R or R' represents a substituted alkyl group it is usually an alkyl group mono-, di- or tri-substituted. Any halogen (i.e. chlorine, fluorine, bromine and iodine) substituent may for example be chlorine, any alkyl substituent may for example be methyl and any alkoxy substituent may for example be methoxy. When there is more than one substituent in any of the groups which R or R' represents, the substituents may be the same or different, e.g. chlorine or methyl.

In a particular embodiment, R represents phenyl; naphthyl; phenyl or naphthyl substituted by one or more substituents selected from halogen, alkyl of 1–4 carbon atoms and alkoxy of 1–4 carbon atoms; alkyl of 1–16 carbon atoms; alkyl of 1–16 carbon atoms substituted by one or more substituents selected from alkoxy of 1–4 carbon atoms, nitro and halogen; phenylalkyl; phenylalkyl whose phenyl group is substituted by one or more substituents selected from halogen and alkyl of 1–4 carbon atoms; a heterocyclic group linked via a carbon atom in the group, the group being a 5 or 6 membered ring containing 1 or 2 hetero atoms, which hetero atoms are selected from nitrogen, oxygen and sulphur, having a benzene ring optionally fused to the 5 or 6 membered ring; or such a heterocyclic group substituted by one or more substituents selected from halogen and alkyl of 1–4 carbon atoms; and R' represents alkyl of 1–6 carbon atoms; alkyl of 1–6 carbon atoms substituted by one or more substituents selected from halogen and alkoxy of 1–4 carbon atoms; phenyl; naphthyl; phenyl or naphthyl substituted by one or more substituents selected from alkyl of 1–4 carbon atoms, alkoxy of 1–4 carbon atoms and halogen; phenylalkyl; or phenylalkyl whose phenyl group is substituted by one or more substituents selected from halogen and alkyl of 1–4 carbon atoms.

In a more particular embodiment, R represents phenyl; phenyl substituted by halogen, alkyl of 1–4 carbon atoms or by alkoxy of 1–4 carbon atoms; alkyl of 1–16 carbon atoms; a heterocyclic group linked via a carbon atom in the group, the group being a 5 or 6 membered ring containing 1 or 2 hetero atoms, which hetero atoms are selected from nitrogen, oxygen and sulphur, having a benzene ring optionally fused to the 5 or 6 membered ring; or such a heterocyclic group substituted by halogen; and Z represents trichloromethylthio.

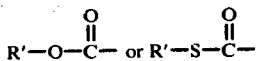

where R' represents alkyl of 1 to 6 carbon atoms. In this more particular embodiment, preferably R represents phenyl, 3-chlorophenyl, 2-chlorophenyl, 3,4-dichlorophenyl, 3-methoxyphenyl, 4-methoxyphenyl, 2-methoxyphenyl, 2,4-dimethylphenyl, 2-methylphenyl, 2,3-dimethylphenyl, 3-methylphenyl, 4-methylphenyl, 2,5-dimethylphenyl, 3,4-dimethylphenyl, 2,6-dimethylphenyl, 4-ethylphenyl, 2-ethylphenyl, 2-pyridyl, 3-pyridyl, 2-benzothiazolyl or 5-chloro-2-pyridyl; and R' represents methyl or ethyl.

In a preferred group of compounds, R represents phenyl; phenyl mono- or di-substituted by chlorine, alkyl of 1-4 carbon atoms or by alkoxy of 1-4 carbon atoms; alkyl of 1-16 carbon atoms; pyridyl; or benzothiazolyl; and Z represents trichloromethylthio.

N-(trichloromethylthio)-anilinomethylenemalononitrile N-(trichloromethylthio)-o-anisidinomethylenemalononitrile, N-(trichloromethylthio)-2,4-xylidinomethylenemalononitrile, N-(trichloromethylthio)-o-toluidinomethylenemalononitrile and S-ethyl (2,2-dicyanovinyl)(m-chlorophenyl)thiocarbamate are particularly good fungicides, e.g. for use on vines.

The present compounds can be prepared by reacting an aminomethylenemalonitrile derivative of formula II with a halide, usually the chloride, of formula ZX in the presence of a base, e.g. sodium ethoxide or potassium ethoxide, or by reacting a salt of the derivative with the halide. The reaction is preferably performed by first forming an alkali metal salt, especially the sodium or potassium salt, of the derivative of formula II, e.g. by treatment with an alkali metal alkoxide, and reacting the salt with the halide.

The reaction is usually conducted by heating, e.g. to a temperature below 100° C, in an inert organic solvent such as toluene.

The present compounds are usually employed in the form of compositions, which can be prepared by a process comprising admixing the ingredients. The compositions are usually produced initially in the form of concentrates, e.g. containing 5–80% of the present compounds, and these are diluted with water or a hydrocarbon, usually water, for application, generally such that the concentration of the present compounds is 0.05–5%. Parts and percentages in this specification are by weight unless otherwise indicated.

The compositions normally contain a surface active agent and/or a carrier.

The carrier may be a liquid, e.g. water (e.g. water used to dilute a concentrate for application). If water is employed as carrier in a concentrate, an organic solvent may also be present as carrier, though this is not usually employed. A concentrate containing water as carrier may advantageously also contain a surface active agent.

The carrier may be a liquid other than water, for example an organic solvent, usually a water-immiscible solvent, e.g. a hydrocarbon which boils within the range 130°-270° C, in which the present compounds are dissolved or suspended. A concentrate containing an organic solvent suitably also contain a surface active agent so that the concentrate acts as a self-emulsifiable oil on admixture with water.

The carrier may be a solid, which may be finely divided. Examples of suitable solids are clays, sand, mica, chalk, attapulgite, diatomite, perlite and sepiolite, and synthetic solid carriers, e.g. silicas, silicates and lignosulphonates.

The carrier may be a fertilizer.

Wettable powders soluble or dispersable in water may be formed by admixing the present compounds with or without a carrier with a surface active agent.

The term 'surface active agent' is used in the broad sense to include materials variously called emulsifying agents, dispersing agents and wetting agents. Such agents are well known in the pesticide art.

The surface active agents used may comprise anionic surface active agents, for example soaps, fatty sulphate esters such as dodecyl sodium sulphate, octadecyl sodium sulphate and cetyl sodium sulphate, fatty aromatic sulphonates such as alkyl-benzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise nonionic surface active agents, for example condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide.

The surface active agents may also comprise cationic surface active agents, for example cetyl trimethylammonium bromide.

Preferred surface active agents include fatty alkyl sulphates, alkyl aryl sulphonates, fatty alkyl ethoxylates, sulphated fatty alkyl ethoxylates, dialkyl sulphosuccinate esters, lignin sulphonate salts, sulphonated naphthalene-formaldehyde condensates and sulphonated urea-formaldehyde condensates.

The composition may be an aerosol composition, containing a propellant which is suitably a polyhalogenated alkane such as dichlorodifluoromethane and usually containing also a solvent.

The present compounds may be admixed with other pesticides for example a herbicide, insecticide or another fungicide, especially another fungicide. Other fungicides with which the compounds may be admixed include N-(trichloromethylthio)cyclohex-4-ene-1,2-dicarboximide, copper compounds, e.g. copper oxychloride or copper sulphate, manganese ethylenebis(-dithiocarbamate), zinc ethylenebis(dithiocarbamate), N-(trichloromethylthio)phthalimide, methyl 2-benzimidazolecarbamate, methyl 1-(butylcarbamoyl)-2-benzimidazolecarbamate, or N-(1,1,2,2-tetrachloroethylthio)cyclohex-4-ene-1,2-dicarboximide.

The compounds are valuable fungicides, and are particularly useful for combating fungal diseases of plants. The compounds may for example be applied to plants, the soil or land. In a preferred embodiment, the compound is applied to a locus at which a crop, particularly a food crop, e.g. potatoes, vines or French beans, is growing or is immediately after application to grow. Especially important is use on vines. The compounds are active against a wide range of fungal diseases including *Phytophthora infestans* (potato blight), *Plasmopara viticola* (vine downy mildew), *Uromyces phaseoli*

(bean rust) and *Botrytis fabae* (chocolate spot). The compounds are usually applied at a rate within the range 0.1–10, e.g. 0.3–3, kg of the compounds per hectare.

The invention is illustrated by the following Examples, in which temperatures are in degrees Centigrade.

EXAMPLE 1

Anilinomethylenemalononitrile (64 parts) was added to a stirred solution of potassium ethoxide (32 parts) in ethanol. The solvent was then evaporated off and the residual potassium salt of anilinomethylenemalononitrile was suspended in toluene (1700 parts). Trichloromethylsulphenyl chloride (65 parts) was added and the mixture heated to 80° for 30 minutes, filtered hot and the filtrate evaporated under reduced pressure. The solid remaining was recrystallised from ethanol to give N-(trichloromethylthio)anilinomethylenemalononitrile (60 parts, 54% yield) as a whitish solid, melting point 135°.

Analysis. —Found: C, 41.50; H, 1.80; Cl, 33.20; N, 13.25; S, 9.90%. $C_{11}H_6Cl_3N_3S$ requires: C, 41.46; H, 1.90; Cl, 33.39; N, 13.19; S, 10.06%.

EXAMPLES 2–17

The following compounds of Formula I in which Z represents trichloromethylthio were prepared by analogous methods to that described in Example 1.

| R | Melting point, degrees |
| --- | --- |
| 2-chlorophenyl | 143 |
| 2-methylphenyl | 116 |
| 2-methoxyphenyl | 105 |
| 2,3-dimethylphenyl | 152 |
| 2,4-dimethylphenyl | 112 |
| 2-pyridyl | 160 |
| 2-benzothiazolyl | 150 |
| 3-methylphenyl | 106 |
| 4-methylphenyl | 130 |
| 2,5-dimethylphenyl | 165 |
| 3,4-dimethylphenyl | 132 |
| 2,6-dimethylphenyl | 122 |
| 4-ethylphenyl | 122 |
| n-tridecyl | 43 |
| 2-ethylphenyl | 63 |
| 3-chlorophenyl | 103 |

EXAMPLE 18 m-Chloroanilinomethylenemalononitrile (70 parts) was added to a stirred solution of potassium ethoxide in ethanol (prepared from 22 parts of potassium hydroxide and 800 parts of ethanol). The solvent was evaporated off and the residual potassium salt of m-chloroanilinomethylenemalononitrile was suspended in toluene (1,700 parts). Ethyl chlorothiolformate (42 parts) was added and the mixture was heated at 80°–90° for 30 minutes and filtered hot. The filtrate was evaporated under reduced pressure to remove the toluene. The solid remaining was recrystallised from ethanol to give S-ethyl (2,2-dicyanovinyl)(m-chlorophenyl)thiocarbamate (63 parts, 63% yield), melting point 68°.

Analysis. —Found: C,53.40; H,3.65; N,14.35%. $C_{13}H_{10}ClN_3OS$ requires: C,53.51; H,3.45; N,14.40%.

EXAMPLES 19–34

The following compounds of general formula I were prepared by reactions analogous to that described in Example 18, Y indicating whether Z is

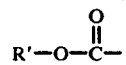

(indicated by 'O') or

(indicated by 'S').

| R | R' | Y | melting point |
| --- | --- | --- | --- |
| 3,4-dichlorophenyl | $C_2H_5$ | S | 145 |
| 3-pyridyl | $CH_3$ | O | 150 |
| 3-pyridyl | $C_2H_5$ | S | 107 |
| 2-pyridyl | $CH_3$ | O | 185 |
| 2-pyridyl | $C_2H_5$ | S | 160 |
| 5-chloro-2-pyridyl | $C_2H_5$ | S | 157 |
| 5-chloro-2-pyridyl | $C_2H_5$ | O | 116 |
| 5-chloro-2-pyridyl | $CH_3$ | O | 165 |
| 3-chlorophenyl | $CH_3$ | O | 154 |
| 3-methoxyphenyl | $CH_3$ | O | 109 |
| 3-methoxyphenyl | $C_2H_5$ | S | 82 |
| 4-methoxyphenyl | $CH_3$ | O | 130 |
| 4-methoxyphenyl | $C_2H_5$ | S | 94 |
| 2,4-dimethylphenyl | $CH_3$ | O | 110 |
| 2,4-dimethylphenyl | $C_2H_5$ | O | 112 |
| 2,4-dimethylphenyl | $C_2H_5$ | S | 172 |

EXAMPLES 35–51

Aqueous suspension containing 500 and 125 parts per million (ppm) of the compounds listed below and 125 ppm of nonylphenol/ethylene oxide condensate as wetting agent were sprayed until the foliage was completely wetted on to young potato plants having seven fully expanded leaves. After 24 hours, the treated plants were inoculated with an aqueous suspension of sporangia of the disease organism potato blight (*Phytophthora infestans*). The plants were then placed in a water saturated atmosphere for 24 hours and then kept in a controlled environment room (temperature 18°, relative humidity 80–90%) for five days after which the incidence of fungal disease was measured. The percentage disease control in comparison with plants identically treated except that they were sprayed with a solution of the wetting agent alone is tabulated below.

| Compound | 500 ppm | 125 ppm |
| --- | --- | --- |
| N-(trichloromethylthio)anilinomethylenemalononitrile | 90 | 70 |
| N-(trichloromethylthio)-o-toluidinomethylenemalononitrile | 98 | 80 |
| Methyl (2,2-dicyanovinyl)(2-pyridyl)carbamate | 90 | 80 |
| S-ethyl (2,2-dicyanovinyl)(m-chlorophenyl)thiocarbamate | 98 | 93 |
| S-ethyl (2,2-dicyanovinyl) (3,4-dichlorophenyl)thiocarbamate | 80 | 75 |
| S-ethyl (2,2-dicyanovinyl)(2-pyridyl)thiocarbamate | 96 | 90 |
| S-ethyl (2,2-dicyanovinyl)(5-chloro-2-pyridyl)thiocarbamate | 85 | 50 |
| N-(trichloromethylthio)-2-chloroanilinomethylene-malononitrile | 80 | |
| N-(trichloromethylthio)-m-toluidinomethylene- | | |

-continued

| Compound | 500 ppm | 125 ppm |
| --- | --- | --- |
| malononitrile | 93 | 85 |
| N-(trichloromethylthio)-p-toluidinomethylene-malononitrile | 92 | 85 |
| N-(trichloromethylthio)-o-anisidinomethylene-malononitrile | 90 | 80 |
| N-(trichloromethylthio)-2,3-xylidinomethylene-malononitrile | 88 | 70 |
| N-(trichloromethylthio)-2,4-xylidinomethylene-malononitrile | 94 | 88 |
| N-(trichloromethylthio)-2,5-xylidinomethylene-malononitrile | 90 | 70 |
| N-(trichloromethylthio)-3,4-xylidinomethylene-malononitrile | 85 | 60 |
| N-(trichloromethylthio)-2,6-xylidinomethylene-malononitrile | 97 | 65 |
| N-(trichloromethylthio)-2-pyridylaminomethylene-malononitrile | 70 | 50 |

EXAMPLES 52–60

Aqueous suspensions containing 125 and 31 ppm of the compounds listed below and 125 ppm of nonylphenol/ethylene oxide condensate as wetting agent were sprayed until the foliage was completely wetted on to young vine plants having five fully expanded leaves. After 24 hours, the treated plants were inoculated with an aqueous suspension of sporangia of the disease organism vine downy mildew (*Plasmopara viticola*). The plants were then placed in a water saturated atmosphere for 12 days after which the incidence of fungal disease was measured. The percentage disease control in comparison with plants identically treated except that they were sprayed with a solution of the wetting agent alone is tabulated below.

| Compound | 125 ppm | 31 ppm |
| --- | --- | --- |
| N-(trichloromethylthio)anilinomethylenemalononitrile | 95 | 95 |
| N-(trichloromethylthio)-o-toluidinomethylenemalononitrile | 90 | 70 |
| S-ethyl (2,2-dicyanovinyl)(m-chlorophenyl)thiocarbamate | 91 | 85 |
| S-ethyl (2,2-dicyanovinyl) (2-pyridyl)thiocarbamate | 75 | |
| N-(trichloromethylthio)-m-toluidinomethylenemalononitrile | 95 | 30 |
| N-(trichloromethylthio)-p-toluidinomethylenemalononitrile | 80 | 30 |
| N-(trichloromethylthio)-2-ethylanilinomethylene-malononitrile | 85 | 35 |
| N-(trichloromethylthio)-o-anisidinomethylenemalononitrile | 96 | 70 |
| N-(trichloromethylthio)-2,6-xylidinomethylenemalononitrile | 97 | 75 |

EXAMPLES 61–64

Aqueous suspensions containing 500 and 125 ppm of the compounds listed below and 125 ppm of nonylphenol/ethylene oxide condensate as wetting agent were sprayed until the foilage was completely wetted on to young bean plants (*Vicia fabae*) having two fully expanded leaves. After 24 hours, the treated plants were inoculated with an aqueous suspension of spores of the disease organism chocolate spot (*Botrytis fabae*). The plants were then placed in a water saturated atmosphere for five days after which the incidence of fungal disease was measured. The percentage disease control in comparison with plants identically treated except that they were sprayed with a solution of the wetting agent alone is tabulated below:

| Compound | 500 ppm | 125 ppm |
| --- | --- | --- |
| N-(trichloromethylthio)anilinomethylenemalononitrile | 80 | 40 |
| N-(trichloromethylthio)-o-toluidinomethylenemalononitrile | 84 | 80 |
| Methyl (2,2-dicyanovinyl)(5-chloro-2-pyridyl)carbamate | 80 | 50 |
| Ethyl (2,2-dicyanovinyl)(5-chloro-2-pyridyl)carbamate | 75 | 45 |

EXAMPLES 65–75

Aqueous suspensions containing the amounts of the compounds listed below and 125 ppm of nonylphenyl/ethylene oxide condensate as wetting agent were sprayed until the foilage was completely wetted on to young French bean plants (*Phaseolus vulgaris*) having two fully expanded leaves. After 24 hours, the treated plants were inoculated with an aqueous suspension of spores of the disease organism bean rust (*Uromyces phaseoli*). The plants were than placed in a water saturated atmosphere for 24 hours and then kept in a controlled environment room (temperature 18° C, relative humidity 80–90%) for 14 days after which the incidence of fungal disease was measured. The percentage disease control in comparison with plants identically treated except that they were sprayed with a solution of the wetting agent alone is tabulated below.

| Compound | 2000 ppm | 500 ppm | 125 ppm |
| --- | --- | --- | --- |
| N-(trichloromethylthio)anilinomethylene-malononitrile | | 80 | 70 |

-continued

| Compound | 2000 ppm | 500 ppm | 125 ppm |
|---|---|---|---|
| N-(trichloromethylthio)-o-toluidino-methylenemalononitrile | | 80 | 70 |
| Methyl (2,2-dicyanovinyl)(2,4-dimethylphenyl) carbamate | 70 | | |
| Methyl (2,2-dicyanovinyl)(4-methoxyphenyl) carbamate | 75 | | |
| Methyl (2,2-dicyanovinyl)(2-pyridyl) carbamate | 80 | | |
| S-ethyl (2,2-dicyanovinyl)(m-chlorophenyl) thiocarbamate | | 70 | |
| S-ethyl (2,2-dicyanovinyl)(3-methoxyphenyl) thiocarbamate | 85 | | |
| S-ethyl (2,2-dicyanovinyl)(4-methoxyphenyl) thiocarbamate | 85 | | |
| S-ethyl (2,2-dicyanovinyl)(2-pyridyl) thiocarbamate | 80 | 55 | |
| S-ethyl (2,2-dicyanovinyl) (3-pyridyl) thiocarbamate | 85 | | |
| S-ethyl (2,2-dicyanovinyl)(5-chloro-2-pyridyl) thiocarbamate | 70 | | |

EXAMPLES 76–80

Wettable powder formulations were prepared by air-milling in a fluid energy mill:

| | |
|---|---|
| N-(trichloromethylthio)anilinomethylenemalononitrile | 25% |
| Sodium salt of sulphonated lignin ('Reax 45L') | 5% |
| China clay | 70% |
| | 100% |
| N-(trichloromethylthio)-o-toluidinomethylenemalononitrile | 25% |
| Sodium salt of sulphonated lignin ('Reax 45L') | 5% |
| China clay | 70% |
| | 100% |
| N-(trichloromethylthio)-o-anisidinomethylenemalononitrile | 25% |
| Sodium salt of sulphonated lignin ('Reax 45L') | 3% |
| Sodium salt of condensate of formaldehyde with a mixture of phenolsulphonic acid and cresolsulphonic acid | 5% |
| Calcined diatomite | 67% |
| | 100% |
| N-(trichloromethylthio)-2,4-xylidinomethylenemalononitrile | 20% |
| Sodium salt of sulphonated lignin ('Reax 45L') | 5% |
| China clay | 75% |
| | 100% |
| S-ethyl (m-chlorophenyl)(2,2-dicyanovinyl)thiocarbamate | 20% |
| Sodium salt of sulphonated lignin ('Reax 45L') | 5% |
| China clay | 75% |
| | 100% |

I claim:

1. An aminomethylenemalononitrile compound of the formula

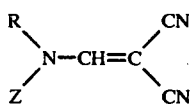 (I)

in which R represents phenyl; naphthyl; phenyl or naphthyl substituted by one or more substituents selected from halogen, alkyl of 1–4 carbon atoms and alkoxy of 1–4 carbon atoms; phenylalkyl; or phenylalkyl whose phenyl group is substituted by one or more substituents selected from halogen and alkyl of 1–4 carbon atoms; and Z represents trichloromethylthio or dichlorofluoromethylthio.

2. A compound according to claim 1 which is N-(trichloromethylthio)-anilinomethylenemalononitrile.

3. A compound according to claim 1 which is N-(trichloromethylthio)-o-toluidinomethylenemalononitrile.

4. A compound according to claim 1 which is (N-trichloromethylthio)-o-anisidinomethylenemalononitrile.

5. A compound according to claim 1 which is N-(trichloromethylthio)-2,4-xylidinomethylenemalononitrile.

6. A compound according to claim 1 wherein R represents phenyl, phenyl substituted by halogen, alkyl of 1 to 4 carbon atoms or alkoxy of 1 to 4 carbon atoms.

7. A compound according to claim 6 wherein R represents phenyl, 3-chlorophenyl, 2-chlorophenyl, 3,4-dichlorophenyl, 3-methoxyphenyl, 4-methoxyphenyl, 2-methoxyphenyl, 2,4-dimethylphenyl, 2-methylphenyl, 2,3-dimethylphenyl, 3-methylphenyl, 4-methylphenyl, 2,5-dimethylphenyl, 3,4-dimethylphenyl, 2,6-dimethylphenyl, 4-ethylphenyl, or 2-ethylphenyl.

8. A compound according to claim 7 wherein R represents phenyl, 2-chlorophenyl, 2-methylphenyl, 2-methoxyphenyl, 2,3-dimethylphenyl, 2,4-dimethylphenyl, 3-methylphenyl, 4-methylphenyl, 2,5-dimethylphenyl, 3,4-dimethylphenyl, 2,6-dimethyl or 4-ethylphenyl.

* * * * *